United States Patent [19]

Yaginuma et al.

[11] Patent Number: 5,081,023
[45] Date of Patent: Jan. 14, 1992

[54] ANTIBIOTIC L53-18A AND PROCESS FOR PREPARATION THEREOF

[75] Inventors: Satoshi Yaginuma; Atsuki Morishita; Naoki Muto; Kenya Ishizawa; Mitsuo Hayashi; Tetsu Saito, all of Shizuoka, Japan

[73] Assignee: Toyo Yozo Company, Ltd., Shizuoka, Japan

[21] Appl. No.: 457,255

[22] Filed: Dec. 27, 1989

[30] Foreign Application Priority Data

Jan. 20, 1989 [JP] Japan ................... 9647/89

[51] Int. Cl.$^5$ ............ C12P 19/62; C12P 17/18; C12N 1/16; C07H 17/08
[52] U.S. Cl. ...................... 435/76; 435/72; 435/74; 435/119; 435/255; 435/911; 536/7.1; 536/7.2
[58] Field of Search ............ 435/76, 252.1, 169, 435/822, 119, 74, 255, 911; 536/7.2, 7.1

[56] References Cited

U.S. PATENT DOCUMENTS

| | | | |
|---|---|---|---|
| 4,251,511 | 2/1981 | Whaley et al. | 435/169 |
| 4,252,898 | 2/1981 | Nash | 435/536 |
| 4,291,021 | 9/1981 | Otani et al. | 435/76 |
| 4,293,651 | 10/1981 | Whaley et al. | 435/169 |
| 4,351,769 | 9/1982 | Whaley et al. | 435/119 |
| 4,482,707 | 11/1984 | Sakakibara et al. | 435/74 |
| 4,935,340 | 6/1990 | Baltz et al. | 435/91 |

FOREIGN PATENT DOCUMENTS

PCT/US90/-01658 10/1990 PCT Int'l Appl.

OTHER PUBLICATIONS

Merck Index, vol. 11, pp. 3624–3625 (1989).
R. Baum, Chemical and Engineering News, p. 6, (Apr. 8, 1991).
J. Lacey et al., J. Gen. Micro., Vol. 88, pp. 75–85 (1975).
Lotvin, G. et al., *J. Antibiot.*, 35:1407–1408, 1982.
Traxler, P., et al., *J. Antibiot.*, 35:594–601, 1982.
Morimoto, K., et al., *J. Antibiot.*, 35:378–380, 1982.
*Index of Antibiotics from Actinomycetes*, 1:2k73, University of Tokyo Press, 1967.
Gherna et al., *ATCC Catalogue of Bacteria and Phages*, 1989, p. 190.

*Primary Examiner*—Ronald W. Griffin
*Assistant Examiner*—Pamela S. Webber
*Attorney, Agent, or Firm*—Darby & Darby

[57] ABSTRACT

A antibiotic L53-18A and a pharmaceutically acceptable salt thereof which are useful for treatment of bacterial inventions are obtained by culturing, for example, *Saccharopolyspora* sp. L53-18 (FERM BP 2231) in a medium and the antibiotic accumulated therein is collected.

1 Claim, 3 Drawing Sheets

ANTIBIOTIC L53-18A AND PROCESS FOR PREPARATION THEREOF

BACKGROUND OF THE INVENTION

The present invention relates to a antibiotic L53-18A produced by actinomycetes Saccharopolyspora sp. L53-18 and a process for producing same.

SUMMARY OF THE INVENTION

The present invention relates to antibiotic L53-18A or its pharmaceutically acceptable salts and a process for producing them, characterized by cultivating actinomycetes Saccharopolyspora sp. L53-18 strain (FERM BP-2231) which produces novel antibiotic (L53-18A) in a culture broth to produce and accumulate said antibiotic (hereinafter referred to as "L53-18A") in the culture broth and collect the antibiotic.

The antibiotic L53-18A of the present invention has the following physicochemical properties.

(1) Color and shape: white powder (2) Molecular formula $C_{37}H_{63}NO_{12}$ (3) Elemental analysis (%):
C: 62.51±1.0, H: 9.38±1.0,
N: 1.89±1.0 (found)
C:62.25, H:8.89, N:1.96 (calcd.)

(4) Molecular weight (FAB-MS method): 714(M+H)$^+$ (5) Distinction of acidic or basic: basic (6) Specific rotary power: $[\alpha]_D^{22} = -37° \pm 10°(C=0.8, chloroform)$ (7) Ultraviolet absorption spectrum: See FIG. 1, Maximum absorption in methanol: $\lambda max = 276\pm 2$ nm ($E_{1cm}^{1\%} = 148\pm 20$).

(8) Infrared absorption spectrum: See FIG. 2 Main wave number (cm$^{-1}$) in potassium bromide tablet: around 3430, 1735, 1690, 1615, 1455, 1370, 1160, 1070 and 1040

(9) Nuclear magnetic resonance ($^1$H-NMR) spectrum: See FIG. 3, (300 MHz in heavy chloroform)

(10) Nuclear magnetic resonance ($^{13}$C-NMR) spectrum: signals (δppm) at 100 MHz in heavy chloroform are recognized below.

204.96(s) 77.93(d) 46.31(d) 21.53(q)
6.00(q) 193.02(s) 77.54(d) 43.05(d)
21.34(t) 175.90(s) 74.76(s) 41.82(t)
21.10(q) 108.58(s) 72.80(s) 40.42(q)
21.01(q) 104.80(d) 70.58(d) 40.42(q)
20.62(q) 96.57(d) 69.69(d) 35.05(t)
17.67(q) 87.14(s) 66.17(d) 31.79(d)
14.06(q) 86.28(d) 64.65(d) 29.13(t)
10 93(q) 78.55(d) 49.29(q) 26.37(q)
10.72(q) (s: singlet, d: doublet, t: triplet, q: quartet)

(11) Solubility: Soluble in methanol, ethanol, acetone, ethyl acetate, chloroform, benzene and acidic water.

(12) Color reaction: Positive to potassium permanganate reaction, iodine reaction, concentrated sulfuric acid reaction, Molisch's reaction, and Dragendorff reaction; negative to ninhydrin reaction, Sakaguchi's reaction, and ferric chloride reaction.

(13) Thin layer chromatography (TLC): spot film, silica gel f (manufactured by Tokyo Kasei Kogyo Co.)

| Solvent | Rf |
|---|---|
| Chloroform-methanol-ammonia water (10:0.5:0.05) | 0.36 |
| Benzene-acetone-ammonia water (5:5:0.1) | 0.29 |
| Ethyl acetate-methanol-ammonia water (10:0.5:0.1) | 0.23 |

Ethyl acetate-methanol-ammonia water (10:0.5:0.1) 0.23

(14) High performance liquid chromatography (HPLC):
Carrier: HITACHI GEL #3056 (manufactured by Hitachi Limited)
Moving bed:Acetonitrile-methanol-1/15M ammonium acetate (50:25:35)
Flow rate:
0.8 ml/min Rt=6.7 (min)

(15) Antimicrobial activity (MIC): Antibacterial spectra for various bacteria are as shown in Table 1.

TABLE 1

| Test bacteria | Minimum growth inhibitory concentration (μg/ml) |
|---|---|
| Staphylococcus aureus FDA 209P JC-1 | 0.20 |
| Staphylococcus epidermidis ATCC 27626 | 0.20 |
| Streptococcus pyogenes N.Y.5 | <0.05 |
| Streptococcus agalactiae 1020 | <0.05 |
| Sarcina lutea ATCC 9341 | <0.05 |
| Bacillus subtilis ATCC 6633 | <0.05 |
| Escherichia coli NIHJ JC-2 | >100 |
| Klebsiella pneumoniae NCTC 9632 | >100 |
| Pseudomonas aeruginosa IAM 1095 | >100 |

(16) Acute toxicity: 300 mg/kg (ip) with surviving mice (10 mice per one group).

DESCRIPTION OF THE INVENTION

Figure 1:
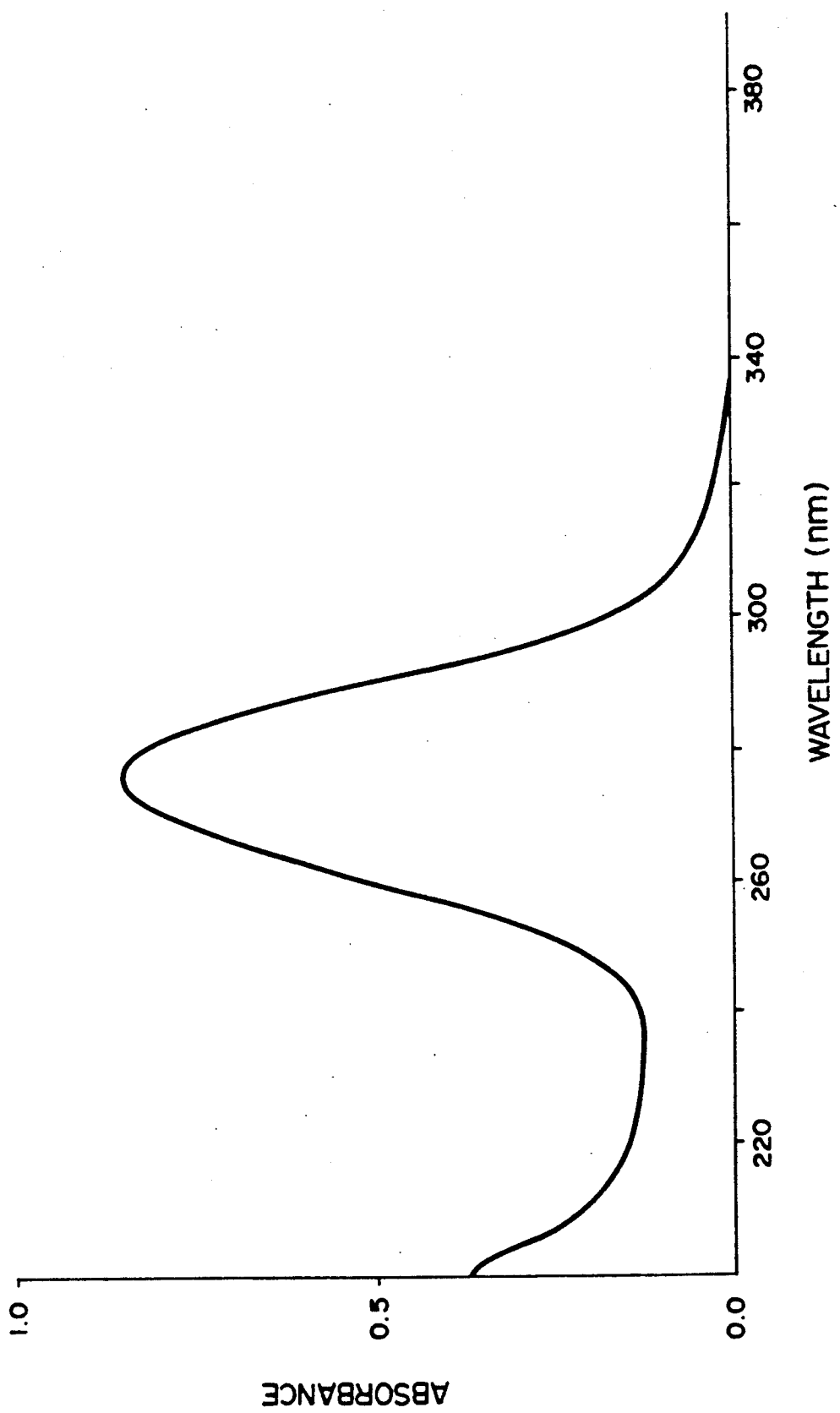
FIGS. 1, 2 and 3 are ultraviolet absorption spectrum, infrared absorption spectrum and nuclear magnetic resonance spectrum ($^1$H-NMR spectrum) of the novel antibiotic L53-18A, respectively.
Figure 2:
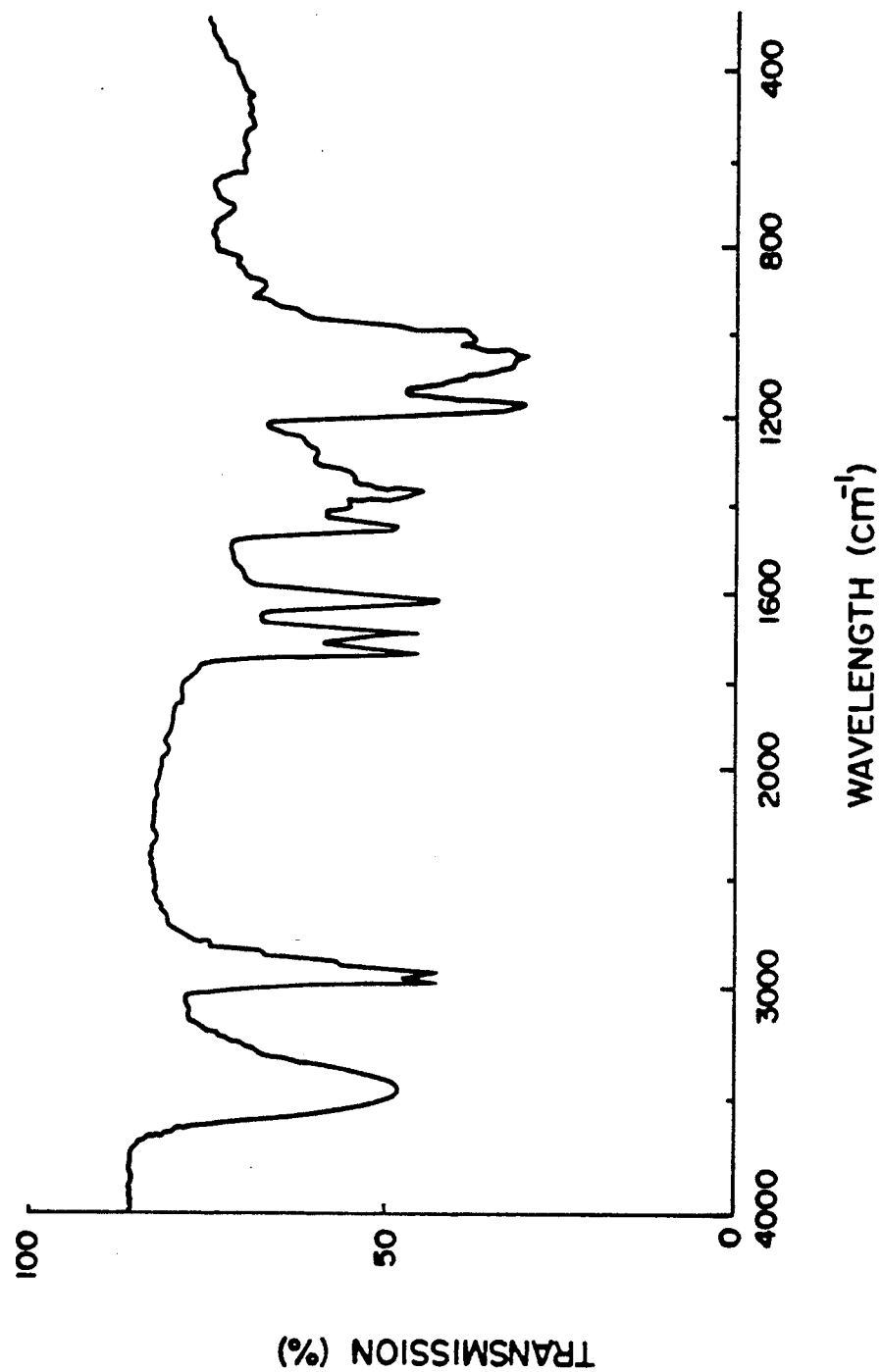
Figure 3:
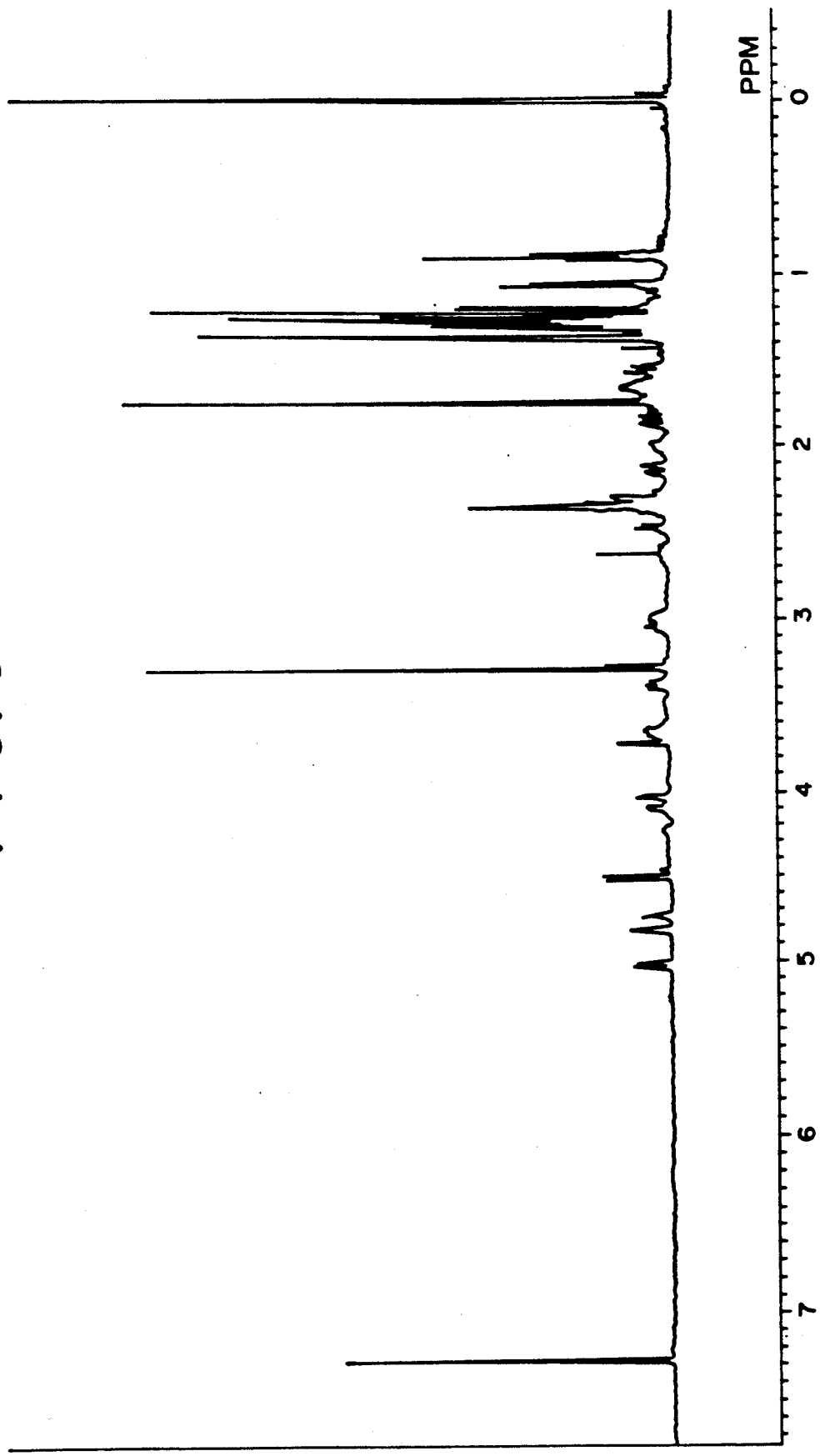

As antibiotics having molecular formula $C_{37}H_{63}NO_{12}$, A-6888X (Japanese Patent Kokai No. 55-154994) and dedesosaminyl 5-0-mycaminosyl-10, 11-dihydromycinamycin IV (J. Antibiot., 35, 1407–1408, 1982) have been known. However, the former has a maximum absorption at 239 nm and the latter has maximum absorptions at 211 nm and 275 nm and these are clearly different from the present antibiotic L53-18A. As antibiotics having a molecular weight of 713, in addition to the above antibiotics, there have been known 16, 17-dihydro-17-hydroxyrifamycin S (J. Antibiot., 35, 594–601, 1982) and anthrimycin C (J. Antibiot., 35, 378–380, 1982) have been known, but molecular formulas of these antibiotics are $C_{37}H_{47}NO_{13}$ and $C_{30}H_{51}N_9O_{11}$, respectively and are clearly different from that of the present antibiotic L53-18A.

The present antibiotic L53-18A is a macrolide antibiotic and has the above-mentioned properties and resemble erythromycin. However, erythromycin has the molecular formula $C_{37}H_{67}NO_{13}$ and shows merely weak ultraviolet ray absorption at 288 nm and can be definitely distinguished from the antibiotic of the present invention. (Index of Antibiotics from Actinomycetes, Vol. 1, page 273, University of Tokyo Press, 1967, Editated by H. Umezawa). Therefore, the antibiotic L53-18A of the present invention is a novel antibiotic.

From the above-mentioned physicochemical properties, the following formula can be mentioned as presumed structural formula of the present antibiotic L53-18A.

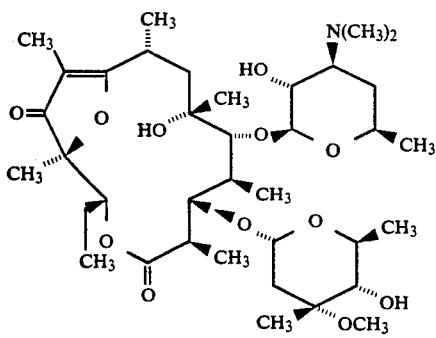

One actinomycetes L53-18 strain suitable to be used for producing the present L53-18A is one isolated from farm soil of Setouchi-cho, Ohshima-gun, Kagoshima-ken (Amamiohshima) and has been identified to belong to genus Saccharpolyspora as a result of strain identification. Its morphological properties, growth of respective culture media and physiological properties are shown below.

I. Morphological properties:

The strain was cultivated on inorganic salts starch agar medium [Inter. J. System, Bacteriol. 16: 313-340 (1966)]at 30° C. for 10-14 days and the results of observation are shown. Nearly the same morphological properties are observed on glycerin asparagine agar, tyrosine agar, oatmeal agar or yeast extract malt extract agar medium. Substrate mycelium is in the form of curved or straight line and grows with formation of branching and forms division in the parts of hyphae or in the later stage of cultivation and has a diameter of 0.4–0.6 μm. Spores are not formed.

Aerial hyphae produced from substrate mycelium are in the form of curved line or straight line and form simple branching and have a diameter of 0.5-0.7μm. The tip thereof is loop-shaped, hook-shaped or spiral-shaped of loose twice widing or in the form of curved line or straight line. The aerial hyphae form arthrospores consisting of many bead-like linkages (normally ten or more) and spaces are often recognized between spores.

The spores are in the ovoidal or short cylindrical form of (0.5–0.7)×(0.7–1.3) μm and observation by transmission electron microscope shows that the spores are covered by coat having many long spiny-processes on the surface.

The substrate mycelium or aerial hyphae do not form sporangium, sclerotium or flagellum spore.

II. Staining: Gram-positive and none acid-fast.

III. Cell Components:

(1) Diaminopimelic acid and sugar Diaminopimelic acid of meso type is detected by analysis according to the method of Staneck et al. [Appl. Microbiol. 28: 226-231 (1974)]and that of LL-type is not detected. Analysis of sugars detects arabinose and galactose but not xylose. Thus, the sugar pattern belongs to type A Inter. J. System. Bacteriol. 20: 435-443 (1970)].

(2) Phospholipid:

According to the method of Minnikin et al [Inter. J. System. Bacteriol. 27: 104-117 (1977)], phosphatidylcholine is detected. Thus, phospholipid type [Biochem. System. Ecol 5: 249-260 (1977)]belongs to PIII type.

(3) Mycolic acid:

According to analysis of lipid by the method of Mordarska et al [J. Gen. Microbiol. 71: 77-86 (1972)], LCN-A is not detected. Analysis by the method of Minnikin et al [J. Gen. Microbiol. 88: 200-204 (1975)]gives neither nocardomycolic acid nor mycolic acid.

(4) Menaquinone:

According to analysis by the method of Collins et al [J. Appl. Bacteriol. 48: 277-282 (1980)], manaquinone (MK) mainly composed of MK-9($H_4$) and MK-10($H_4$) is detected.

IV. Properties in cultivation:

Cultivation is carried out on various culture media at 30° C. for 20 days and results of observation are shown in Table 2. Indication of colors is in accordance with "Color Harmony Manual", the fourth edition, 1958 (Container Corporation of America).

TABLE 2

| Properties in cultivation on various culture media L53-18 strain | | | | |
|---|---|---|---|---|
| Culture media | Growth | Substrate mycelium | Aerial hyphae | Soluble pigment |
| Sucrose.nitrate agar | Good | Copper Brown (5 pi) | Good; powdery, Light Fawn (4 ge) to Bisque (4 ec) | Copper.Brown (5 pi) |
| Glucose.asparagine agar | Poor | Colorless or Light Ivory (2 ca) | None | None |
| Glycerine.asparagine agar | Good to medium | Cinnamon (3 le) | Good or medium; powdery, Light Fawn (4 ge) to Bisque (4 ec) | Dark Luggage Tan (4 pg) |
| Inorganic salts starch agar | Good to medium | Cinnamon (3 le) | Good to medium; powdery, Light Fawn (4 ge) to Bisque (4 ec) | Dark Luggage Tan (4 pg) slightly |
| Tyrosine agar | Good | Oak Brawn (4 pi) | Good; powdery, Light Fawn (4 ge) to Bisque (4 ec) | Copper Brown (5 pi) |
| Oatmeal agar | Good to medium | Light Tan (4 gc) | Good to medium; powdery, Light Fawn (4 ge) to Bisque (4 ec) | Nude Tan (4 gc) |
| Yeast extract. malt extract agar | Good | Oak Brown (4 pi) | Good; powdery, Light Fawn (4 ge) to Bisque (4 ec) | Copper Brown (5 pi) |
| Nutrient agar | Medium | Light Wheat (2 ea) | Poor; White (a) to Pearl (3 ba) | None |
| Glycerine nitrate agar | Good | Oak Brown (4 pi) | Good; powdery, Light Fawn (4 ge) to Bisque (4 ec) | Copper Brown (5 pi) |
| Bennett's agar | Good | Oak Brown (4 pi) | Good; powder, Light Fawn (4 ge) to Bisque (4 ec) | Oak Brawn (4 pi) |
| Emerson's agar | Good | Cinnamon (3 le) | Medium to good; powdery, Light Fawn (4 ge) to Bisque (4 ec) | Oak Brawn (4 pi) |
| Hickey and | Good | Oak Brawn (4 pi) | Good; powdery, Light Fawn (4 ge) to Bisque | Copper Brown |

TABLE 2-continued
Properties in cultivation on various culture media L53-18 strain

| Culture media | Growth | Substrate mycelium | Aerial hyphae | Soluble pigment |
|---|---|---|---|---|
| Tresner's agar | | | (4 ec) | (5 pi) |

V. Physiological properties:

(1) Range of growing temperature: 24°-25° C., most suitable 28°-35° C.

(2) Gelatin liquefaction: positive (3) Hydrolysis of starch: positive (4) Peptonization of skim milk: positive Coagulation of skim milk: doubtful (5) Production of melanin pigment: On tyrosine agar medium: negative On peptone yeast extract iron agar medium: negative (6) Demand for oxygen: aerobic (7) Production of hydrogen sulfide: positive (8) Resistance to lysozyme: sensitive [Inter. J. System. Bacteriol. 27: 176-178 (1977)]

(9) Resistance to sodium chloride: Growing at 0-10%, but not growing at 11% or more. (ISP medium 2 was used as basal medium).

(10) Resistance to antibiotic: as shown in Table 3. [according to J. Antibiot. 32: 180-186 (1976)]

TABLE 3

| Antibiotics | MIC ($\mu$g/ml) | Antibiotics | MIC ($\mu$g/ml) |
|---|---|---|---|
| Kanamycin | 63 | Neomycin | 63 |
| Gentamicin | 16 | Spectinomycin | >1000 |
| Paromomycin | 31 | Rifampicin | <16 |
| Streptomycin | 31 | Leucomycin A5 | >1000 |

(11) Resolving power of various substances:

TABLE 4

| Substances | Resolving power | Substances | Resolving power |
|---|---|---|---|
| Tyrosine | + | Adenine | + |
| Casein | + | Aesculin | + |
| Xanthine | + | Keratin | − |
| Hypoxanthine | + | Elastin | + |
| Cellulose | − | Urea | + |

[According to Gray et al. Ecology of soil bacteria, p293-321, Liverpool University Press, 1967, J. Gen. Microbiol. 69: 33-38 (1971) and J. Gen. Microbiol. 88: 75-85 (1975)]

(12) Utilization of carbon source;

(a) Sugars (ISP medium 9 was used as basal medium)

TABLE 5

| Sugars | Utilization | Sugars | Utilization |
|---|---|---|---|
| L-arabinose | + | D-ribose | + |
| D-fructose | + | Trehalose | + |
| D-galactose | + | Sucrose | + |
| D-glucose | + | L-sorbose | − |
| Glycerin | + | D-sorbitol | + |
| Inositol | + | Dulcitol | − |
| D-mannitol | + | D-xylose | + |
| D-mannose | + | Salicin | |
| Melezitose | + | Cellobiose | + |
| Melibiose | + | Starch | + |
| $\beta$-Lactose | − | Adonitol | + |
| Maltose | + | Erythritol | + |
| Raffinose | + | $\alpha$-Methyl-D-glycoside | − |
| L-rhamnose | + | Cellulose | − |

(b) Organic acid [according to J. Bacteriol. 73: 15-27 (1957)]

TABLE 6

| Organic acids | Utilization | Organic acids | Utilization |
|---|---|---|---|
| Sodium acetate | + | Sodium propionate | + |
| Sodium benzoate | + | Sodium succinate | + |
| Sodium butyrate | + | Sodium tartrate | − |
| Sodium citrate | + | Adipic acid | + |
| Sodium fumarate | + | Sodium pyruvate | + |
| Sodium malate | + | Sebacic acid | + |

As shown above, L53-18 strain has the following features.

(1) Morphologically, it produces aerial hyphae which form many spore chains from substrate mycelium having divisibility and does not form flagella spores or sporangia.

(2) Regarding cell components, diaminopimelic acid is meso type, sugar pattern* is A type, phospholipid** is PIII type, nocardomycolic acid or mycolic acid is not contained and menaquinone (MK) is mainly composed of MK-9($H_4$) and MK-10($H_4$).

* Classification by Lechevalie et al [Inter. J. System, Bacteriol., 20: 435-443(1970)].
** Classification by Lechevalie et al [Biochem. System. Ecol., 5: 249-260 (1977)].

Thus, L53-18 strain belongs to genus Saccharopolyspora Lacey and Goodfellow and is named Saccharopolyspora sp. L53-18 (refer to J. Gen Microbiol. 88: 75-85 (1975). This strain is deposited as FERM BP-2231 at Fermentation Research Institute, Agency of Industrial Science and Technology, Japan.

The present antibiotic L53-18A is obtained in the following manner in accordance with a process for producing antibiotics. That is, mutants or variants of microorganisms which have ability to produce antibiotic L53-18A in a collectable amount are aerobically cultivated in a culture medium containing components used for cultivation of microorganisms. Cultivation is usually conducted in a liquid medium. Aerated submerged culturing procedure is industrially advantageous. The above antibiotic is produced and accumulated in the cultured broth and the antibiotic is collected from cultured broth.

As nutrients for culture medium, there may be widely used those which are ordinarily used for culture of microorganisms. For example, glucose, dextrin, sucrose, starch, fructose, maltose, blackstrap molasses, fatty oils, and organic acids are used as carbon sources and soybean powder, cotton seed powder, corn steep liquor, meat extract, yeast extract, peptone, ammonium sulfate and urea are used as nitrogen sources. Furthermore, if necessary, there may be added salts such as sodium chloride, potassium chloride, calcium carbonate, magnesium sulfate, potassium dihydrogen-phosphate, disodium hydrogenphosphate, ferrous sulfate, cupric sulfate, zinc sulfate, and cobalt chloride, and heavy metal salts, vitamins, anti-foam agents, and amino acids.

Cultivation conditions may be optionally varied as far as the strain can grow and produce the antibiotic. For example, cultivation temperature is 24°-25° C., preferably 28°–35° C., pH is 5.0–9.5, especially about 7.0 and cultivation day is 2–8 days, normally 4–7 days.

The present antibiotic L53-18A is basic and organic solvent-soluble and is present mainly in filtrate and so one embodiment of isolation and collection of the antibiotic L53-18A from culture comprises first subjecting the culture broth to filtration and centrifugal separation to remove the mycelial cake, extracting the resulting filtrate with a non-water-soluble solvent at a pH of alkline side and concentrating the extract to obtain a crude antibiotic. The non-water-soluble solvents used for extraction include, for example, ethyl acetate, butyl acetate, butanol, and chloroform. Furthermore, the extractant can be adsorbed to synthetic adsorbents, for example, resins such as DIAION HP-20, then eluted with water-containing alcohol or the like and concentrated to obtain the crude antibiotic. For further purification, column chromatography using silica gel, activated alumina, etc. is suitable. As solvents for elution, chloroform, ethyl acetate, benzene, methanol, acetone, ammonia water and the like are used singly or in combination of them.

Since L53-18A has antibacterial activity, assay thereof can be performed by measuring antibacterial activity by bioassay with suitable assay bacteria such as *Sarcina lutea* as used for general antibiotics and carrying out quantitative determination.

If necessary, the present anitibiotic may be used in the form of pharmaceutically acceptable nontoxic salts, for example salts with inorganic acids such as hydrochloric acid and sulfuric acid and organic acids such as acetic acid, malic acid, gluconic acid, citric acid, glutamic acid and aspartic acid.

The following nonlimiting examples will further explain the present invention. "%" in these examples is by weight unless otherwise notified.

EXAMPLE 1

A culture medium containing 1.0% of glucose, 1.0% of dextrin, 0.5% of casein hydrolyzate, 0.5% of yeast extract and 0.1% of calcium carbonate was used as a seed medium. A culture medium containing 2.5% of dextrin, 1.2% of Ebios, 2.0% of corn steep liquor, 0.1% of sodium bromide and 0.001% of cobalt chloride was used as a production medium. Both the media were adjusted to pH 6.5 before sterilization.

Saccharopolyspora sp. L53-18 strain (FERM BP-2231) which was sufficiently grown in oatmeal agar slant was inoculated in two of 500 ml conical flasks which contained 100 ml of the above seed medium which had been sterilized and these flasks were shaken at 28° C. for 3 days. These were referred to as the first seed cultures. Then, 200 ml of the first seed culture was inoculated in one jar fermentor of 30 liter which contained 20 liters of sterilized seed culture medium. The cultivation was performed at 28° C. for 2 days with aeration (20 l/min.) and agitation (200 rpm). The resulting culture broth was referred to as the second seed culture.

Then, this second seed culture was inoculated in one culture tank of 250 liters which contained 200 liters of the sterilized production culture medium. Fermentation was carried out at 28° C. for 4 days with aeration (160 l/min.) and agitation (150 rpm).

After completion of cultivation, filtration was carried out using diatomaceous earth to obtain 200 liters of culture filtrate. Production amount of L53-18 A in this case was about 10 μg/ml according to bioassay conducted using *Sarcina lutea* ATCC9341 as bacterium for assay.

EXAMPLE 2

Filtrate (220 liters) obtained in Example 1 was adjusted to pH 8.0 with sodium hydroxide and was subjected to extraction with 120 liters of ethyl acetate to obtain 100 liters of ethyl acetate solution containing desired product. Then, 70 liters of water was added to the extract and extraction was carried out with adjusting the pH to 4.5 with hydrochloric acid to transfer and dissolve the extract into aqueous layer. This aqueous layer was adjusted to pH 8.0 with ammonia water and then extracted with 30 liters of chloroform to transfer and dissolve the desired product into the chloroform layer. The chloroform layer was concentrated under reduced pressure to obtain about 50 g of yellowish brown crude substance.

The resultant substance was dissolved in a small amount of ethyl acetate and the solution was charged in a silica gel column (1.5 liter) previously filled with ethyl acetate and washed with 3 liters of ethyl acetate and thereafter eluted with a mixture of ethyl acetate-methanol-ammonia water (10:0.5:0.1) and fractionated into 400 ml each. Fraction Nos. 24–35 were collected, concentrated under reduced pressure, then charged in a silica gel column (250 ml) filled with a mixture of chloroform-methanol-ammonia water (10:0.2:0.02) and eluted with a mixture of chloroform-methanol-ammonia water (10:0.3:0.03). The desired product was confirmed by antibacterial activity measured using *Sarcina lutea* ATCC9341 and by silica gel thin layer chromatography with developer solvent chloroform-methanol-ammonia water (10:0.5:0.05) and fractions containing only L53-18A were collected and concentrated to dryness under reduced pressure to obtain 620 mg of white powder of L53-18A.

EXAMPLE 3

0.05M aqueous citric acid solution was added to 50 mg of the white powder obtained in Example 2 to dissolve the powder and the solution was adjusted to pH 7.0 and lyophilized to obtain white powder of citrate of the present antibiotic L53-18A. The white powder obtained in Example 2 was dissolved in aqueous hydrochloric acid of pH 4.0 and the solution was adjusted to 7.0 and lyophilized to obtain white powder of hydrochloride of the present antibiotic L53-18A.

The novel antibiotic L53-18A or its pharmaceutically acceptable salt shows antibacterial activity to Gram-positive bacteria and so this antibiotic or salt formulated can be utilized as antibiotic for treatment of bacterial infections by oral or parenteral administration of it to human beings and domestic animals and fowls like general antibiotics.

We claim:

1. A process for producing antibiotic L53-18A having the structure

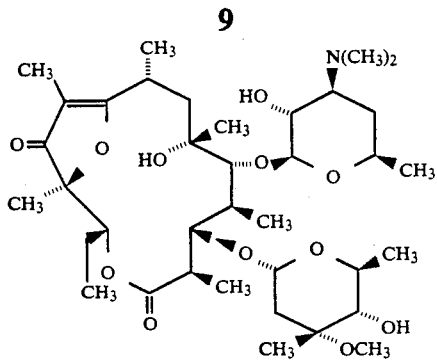
which comprises cultivating Saccharopolyspora sp. L53-18A, having the identifying characteristics of FERM BP-2231, in an aqueous nutrient medium under aerobic conditions until antibiotic L53-18A accumulates in said medium and collecting antibiotic L53-18A from said medium.
* * * * *